US00PP10335P

United States Patent [19]

LeBoutillier

[11] Patent Number: Plant 10,335

[45] Date of Patent: Apr. 21, 1998

[54] *TAXUS CUSPIDATA* CV. 'MONLOO'

[75] Inventor: Roberts LeBoutillier, Exton, Pa.

[73] Assignee: Monrovia Nursery Company, Azusa, Calif.

[21] Appl. No.: 710,932

[22] Filed: Sep. 26, 1996

[51] Int. Cl.[6] ..... A01N 5/00

[52] U.S. Cl. ..... Plt./50.3

[58] Field of Search ..... Plt./50.3

[56] References Cited

U.S. PATENT DOCUMENTS

P.P. 2,052 4/1961 Wyman, Jr. ..... Plt./50.3

P.P. 4,802 1/1982 Hill ..... Plt./50.3

*Primary Examiner*—James R. Feyrer

*Assistant Examiner*—Kent L. Bell

[57] ABSTRACT

A new and distinct selection of Japanese Yew, *Taxus cuspidata*, which shall be referred to hereinafter as 'Monloo'. 'Monloo' differs distinctively from other *Taxus cuspidata* plants by its unique combination of small dense needles, symmetrical low growth, shorter rigid branching, and a comparatively overall enhanced denser appearance. This uniquely compact and dense plant requires less pruning than other Japanese yews having horizontal growth habits due to its dense branching, and can be maintained as a small foundation specimen or can be planted in rows to form a thick, dense hedge.

1 Drawing Sheet

BACKGROUND OF THE INVENTION

This invention relates to a new and distinct selection of *Taxus cuspidata*, a member of the Taxaceae family. *Taxus cuspidata* cultivar 'Monloo' was discovered as a sport of *Taxus cuspidata* around the year 1970. My sport was initially detected and propagated as it exhibited short dense uniform needles and later was observed to retain a symmetrical low growth habit. My new plant has been asexually reproduced by cuttings since the discovery at Waterloo Nursery 200 N. Whitford Road, Exton, Pa. and later at Monrovia Nursery Company, 13455 S.E. Lafayette Highway, Dayton, Oreg. The parent *Taxus cuspidata* of my sport has an ascending wide spreading growth habit which can achieve a height of more than 3 meters.

Growth is irregular and branching appears loose and floppy. My discovery does not get taller than 75 cm and has a rigid symmetrical branching habit.

My discovery substantially differs from its parent *Taxus cuspidata* in having small, dense needles, and a symmetrical low growth and rigid branching and a comparatively overall enhanced denser appearance. These characteristics set the claimed plant apart from the parent *Taxus cuspidata* and other cultivars of *Taxus cuspidata* which I am aware. Had the initial sport not been discovered and successfully separated and rooted by me it may have been lost to mankind. It is unlikely the favorable attributes of this plant could be conveyed to progeny through sexual reproduction. However, through extensive propagation by rooting of cuttings of this plant it has been established that the novel, exceptional characteristics of this plant are stable and reliably passed on to clonal specimens through asexual reproduction.

SUMMARY OF INVENTION

*Taxus cuspidata* cv. 'Monloo' is the lowest spreading Japanese Yew to my knowledge. The ultimate height will remain under 75 cm.

This dwarf plant adapts easily to pruning to limit width or to form into other shapes. Typically *Taxus cuspidata* has loose floppy unsymmetrical branching. *Taxus cuspidata* cv. 'Monloo' has shorter rigid, symmetrical branching. Annual branch growth from plants grown in Oregon at the same location is 8–14 cm for cv. 'Monloo' compared to 19–35cm for *Taxus cuspidata*. Terminal growth from plants grown in Oregon at the same location is 9–20 cm for cv. 'Monloo' compared to 34–50 cm for *Taxus cuspidata*.

Other low growing yews do exist however these are the *Taxus baccata* cultivars which tolerate a –10 F temperature and are not as cold hardy as *Taxus cuspidata* cv. 'Monloo' which can tolerate a –30° F. 'Monloo' requires less pruning while forming an unusually dense, compact plant which is adapted for foundation or hedge forming plantings. This plant may require no pruning yet mature into an attractive specimen of natural appearance with unusual density and symmetry.

BRIEF DESCRIPTION OF DRAWINGS

The photograph of the discovery shows an approximately 3 year old plant which exhibits a dense symmetrical habit and height of approximately 20 cm. It does not display the wide spreading habit which is visible in mature plants.

BOTANICAL DESCRIPTION

Below is a detailed description of my selection of *Taxus cuspidata* cv. 'Monloo', the color terminology is from the British Horticultural Color Charts (Wilson) and The *Royal Horticultural Society Colour Chart*.

Overall size: Low spreading habit achieving an ultimate size in 20 years of 75cm tall and more than 3 meters in width.

Overall habit: Evergreen conifer, low growing shrub, symmetrical, rigid branching, short closely spaced foliage gives a dense compact appearance.

Flowers: Female clone.

Fruit: Seeds surrounded by a red aril.

Foliage (needles):

*Shape*.—Linear abruptly accuminate with a small soft mucronulate tip.

*Cross section*.—Slightly keeled, flat on cross section.

*Size*.—10–16 mm in length, 2–3 mm in width.

*Arrangement*.—Irregularly 2 ranked to radically arranged usually needles not on bottom half of branch.

*Color.*—Mature, upper surface: Ivy Green 0001060 or Green Group 139A. Mature, lower surface: Spinach Green 0960/1 or Yellow-Green Group 144A.

*Petiole.*—Fern green 0862.

*Texture.*—Leathery .

Bark:

*Mature growth.*—Mixture of Garnet Brown 00918/3 and Mars Orange 013 or Greyed-Orange Group 174A.

*Young growth.*—Fern green 0862 or Yellow-Green 144–A144B.

*Texture.*—Smooth, glaborous.

General Observation:

While the characteristics of this new plant 'Monloo' are quite similar to those seen in previously introduced spreading varieties within the species, the dimensions of the parts of this plant are a miniature version of those of known plants. Culturing this plant is possible in locations which would soon be overgrown by market available varieties of similar growth habit but having longer plant parts. Further, this plant has:

1. This plant has 10 needles per centimeter while the parent has 5. This gives a finer texture which is starkly attractive.

2. While branching pattern is about the same as that of the parent, the reduced plant part dimensions of this plant result in a much more condensed version.

3. Cuttings root with an expectation of 86%; this plant is more difficult to root than other named varieties within the same species.

4. This plant does well in full sun and under shaded conditions; does not suffer from sun scald in direct sun.

I claim:

1. A new and distinct selection of *Taxus cuspidata* plant as substantially shown and described herein, that is characterized particularly as a novelty by the unique combination of small dense needles and a symmetrical low growth and shorter rigid branching and a comparatively overall enhanced denser appearance.

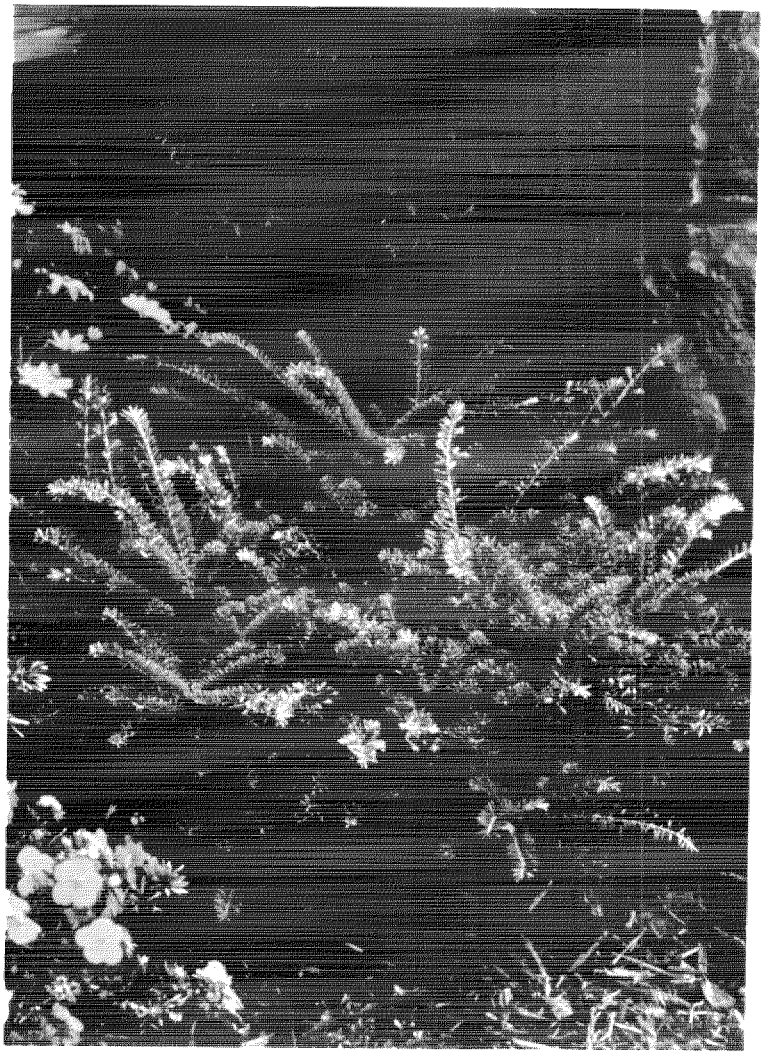

* * * * *